United States Patent
Ishikawa (10) Patent No.: US 6,815,384 B2
(45) Date of Patent: Nov. 9, 2004

(54) METHOD FOR MANUFACTURING SINTERED PIECE (75) Inventor: Tsuyoshi Ishikawa, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/290,160

(22) Filed: Nov. 8, 2002

(65) Prior Publication Data

US 2003/0176268 A1 Sep. 18, 2003

(30) Foreign Application Priority Data

Nov. 13, 2001 (JP) ......................................... 2001-347984

(51) Int. Cl.$^7$ ...................... C04B 35/057; C04B 35/447
(52) U.S. Cl. ............................ 501/1; 264/43; 264/648; 264/673; 264/675
(58) Field of Search ............................... 501/1; 264/43, 264/648, 673, 675

(56) References Cited

U.S. PATENT DOCUMENTS

| | | | |
|---|---|---|---|
| 4,113,500 A | 9/1978 | Ebihara et al. | 501/1 |
| 4,149,894 A | 4/1979 | Ebihara et al. | 501/111 |
| 4,230,455 A | 10/1980 | Hidaka et al. | 433/202.1 |
| 4,654,314 A * | 3/1987 | Takagi et al. | 501/82 |
| 4,767,583 A | 8/1988 | van der Meer et al. | 264/656 |
| 4,919,751 A | 4/1990 | Sumita et al. | 216/56 |
| 4,957,674 A | 9/1990 | Ichitsuka et al. | 264/654 |
| 4,963,145 A * | 10/1990 | Takagi et al. | 606/76 |
| 5,018,847 A | 5/1991 | Ojima et al. | 359/398 |
| 5,718,855 A | 2/1998 | Akahori et al. | 264/122 |
| 6,235,225 B1 * | 5/2001 | Okada et al. | 264/44 |

FOREIGN PATENT DOCUMENTS

| | | |
|---|---|---|
| GB | 2142919 | 1/1995 |
| JP | 6-144918 | 5/1994 |
| JP | 2657403 | 6/1997 |
| JP | 2001-163662 | 9/2001 |
| JP | 2001259017 | 9/2001 |
| JP | 2003-047461 | 2/2003 |

OTHER PUBLICATIONS (2) English Language Abstracts of JP Appln. No. 2001–259017.
(2) English Language Abstracts of JP Appln. No. 6–144918.
English Language Abstract of JP 2003–047461, Feb. 18, 2003.

* cited by examiner

*Primary Examiner*—Karl Group
(74) *Attorney, Agent, or Firm*—Greenblum & Bernstein, P.L.C.

(57) ABSTRACT

The method for manufacturing a sintered piece comprises preparing a molded piece of a composite including calcium phosphate compound such as hydroxyapatite, and baking the molded piece in an oxygen atmosphere to obtain the sintered piece. The oxygen concentration of the oxygen atmosphere is controlled to be not less than 25 vol %, and the relative humidity of the oxygen atmosphere is controlled to be below 30% RH. The baking is performed for 30 minutes to 8 hours at a temperature not less than 1000° C. and below a temperature at which thermal decomposition of the calcium phosphate occurs.

17 Claims, 5 Drawing Sheets

METHOD FOR MANUFACTURING SINTERED PIECE

BACKGROUND OF THE INVENTION

The present invention relates to a method for manufacturing a sintered piece, and in particular, to a method for manufacturing a sintered piece including calcium phosphate compound.

Hydroxyapatite is a kind of calcium phosphate ceramics (calcium phosphate compound) and is a main constituent of bones and tooth. Thus, hydroxyapatite is used as biomaterial for an artificial bone, an artificial dental root, and medical/dental cement, for example. That is, hydroxyapatite is shaped to a desired form by means of molding, and then baked to obtain a sintered piece of hydroxyapatite which is usable as the artificial bone or dental root.

When it is used as the artificial bone or dental root, the sintered piece of the hydroxyapatite is required to have both high mechanical strength and good bio-compatibility. The mechanical strength of the sintered piece can be enhanced by increasing the relative density thereof. However, the bio-compatibility of the sintered piece decreases with the increase of the relative density of the sintered piece, and vice versa, since the growth of the osteoblast into the sintered piece becomes more difficult with the increase of the relative density thereof.

Therefore, there was a demand for a method for increasing the mechanical strength of the sintered piece of hydroxyapatite without increasing its relative density.

SUMMARY OF THE INVENTION

The present invention is advantageous in that it provides a method for manufacturing a sintered piece including calcium phosphate compound and has high mechanical strength but low relative density.

According to an aspect of the invention, there is provided a method for manufacturing a sintered piece in which a molded piece of a composite including calcium phosphate compound such as hydroxyapatite is prepared and then baked in an oxygen atmosphere to obtain the sintered piece. The oxygen concentration of the oxygen atmosphere is controlled to be not less than 25 vol %. Optionally, the relative humidity of the oxygen atmosphere is controlled to be below 30% RH. The baking is performed for 30 minutes to 8 hours at a temperature not less than 1000° C. but below a temperature at which thermal decomposition of the calcium phosphate occurs. The sintered piece obtained as above has high mechanical strength with low relative density thereof.

Optionally, at least a part of the molded piece is covered with a sinter assisting material, during the baking, that enables efficient heating of the covered part of the molded piece to increase the mechanical strength thereof. It is found that powder, in particular that having average particle diameters of 3 to 300 µm, is suitable for the sinter assisting material since such powder allows the gas surrounding the molded piece to be exchanged and in turn the atmosphere around the molded piece to be uniform.

A material of which main component is calcium phosphate compound is suitable for the sinter assisting material since the bio-compatibility of the sintered piece will not be affected even if such a sinter assisting material has contaminated or adhered to the sintered piece. The sinter assisting material is preferably pre-baked in advance of the baking of the molded piece at a temperature not less than the temperature of the baking to deactivate the sinter assisting material.

Optionally, the molded piece is pre-baked in advance of the baking, or main baking. The pre-baking may be performed under different condition from that of the main baking of the molded piece. For example, the pre-baking may be performed in air atmosphere to reduce the manufacturing cost of the sintered piece.

DETAILED DESCRIPTION OF THE EMBODIMENTS

Hereinafter, a manufacturing method of a sintered piece according to an embodiment of the present invention will be described with reference to the accompanying drawings.

Figure 1:
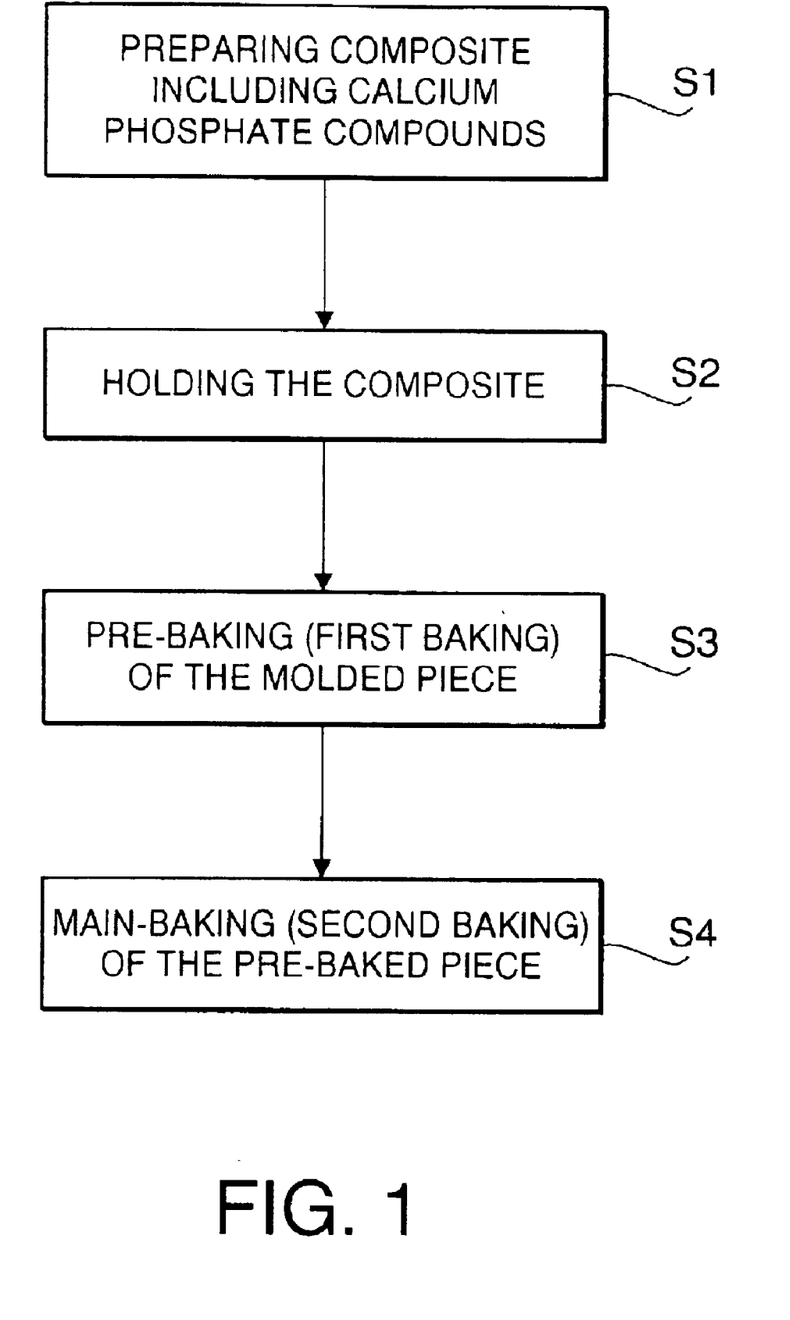
FIG. 1 is a flow chart showing a manufacturing process of a sintered piece according to an embodiment of the invention.

FIG. 1 is a flow chart showing a manufacturing process of a sintered piece according to an embodiment of the invention.

The sintered piece manufacturing method shown in FIG. 1 includes the following four steps (S1–S4).

[Step S1]

In this step, a composite including calcium phosphate compounds is prepared. Calcium phosphate includes, for example, apatites such as hydroxyapatite, fluorapatite, and carbonate-apatite, dicalciumphosphate, tricalciumphosphate, tetracalciumphosphate, and octacalciumphosphate. A mixture of one or more of the above may be used for preparing the composite. It should be noted that hydroxyapatite is most preferable among the materials above since the sintered piece obtained therefrom has excellent bio-compatibility and is useful as artificial bones and dental roots.

The composite may be provided in a variety of forms including powder, paste obtained by mixing the powder with liquid, and slurry. The average diameter of the particles of the powder is preferably in a range of 1 to 200 µm, and more preferably in a range of 3 to 30 µm. By using powder having such an average particle diameter, the sintered piece becomes to have sufficiently small relative density, or sufficiently large void content.

[Step S2]

In this step, the composite prepared in step S1 is molded. As described before, the composite to be molded may be provided as powder, paste, or slurry, for example.

If the composite is provided in the form of powder, the composite may be formed into a predetermined shape by being placed in a molding tool and then pressed (powder pressing molding).

If the composite is provided in the form of paste, it may be formed by being brought into the molding tool and dried. It should be noted that a viscosity bodying agent, such as methylcellulose, may be mixed into the composite so that it can be gelled by introducing bubbles therein before being brought into the molding tool. In this case, the drying temperature may be set to a temperature by which the composite can keep its gelled state.

If the composite is provided as slurry, the solid phase of the slurry is formed by being unevenly distributed in the molding tool by means of settlement or centrifuge, or by being left in the molding tool by means of dewatering.

The molding temperature is preferably controlled within a range of 10 to 70° C., and normally it is controlled to about the room temperature. It should be noted, however, the molding temperature is not limited to the range mentioned above.

A mold release agent may be applied to the inner surface of the molding tool to facilitate the taking off of the molded piece from the molding tool. Liquid paraffin and various kinds of wax may be used as the mold release agent. In particular, agents that decompose and disappear due to heat during baking processes in the following steps S3 and S4 are preferable since such agents do not remain in the sintered piece and hence do not deteriorate the safety of the sintered piece against a living body.

It should be noted, however, the mold release agents that can be utilized are not limited to the materials mentioned above.

The molded piece obtained in the molding tool may be further dried, if it is necessary, by means of vacuum drying, air-drying, freeze-drying, or the like. Then, the molded piece is taken out from the molding tool. The mold release agent applied on the inner surface of the molding tool allows the molded piece to be taken out from the molding tool without deforming and getting damages.

Note that the molding tool may be divided in several pieces when the molded piece is to be removed therefrom.

The molded piece taken out from the molding tool may be provided to the next step S3 without applying any additional process, or, after being shaped by, for example, slicing, cutting, grinding, or polishing.

The shape and dimensions of the molded piece is decided in accordance with the shape and dimensions of the desired sintered piece and also by taking into account the shrinkage of the molded piece during the baking process in the following steps S3 and S4.

[Step S3]

In this step, pre-baking (first baking) of the molded piece prepared in the previous step S2 is performed. This pre-baking process provides the following advantages.

<1> The pre-baking reduces the manufacturing cost of the sintered piece. A main baking (second baking) of the following step S4 is performed by an atmospheric furnace of which running costs is relatively high. Accordingly, the time required for the main baking should be reduced from the viewpoint of the manufacturing cost. The pre-baking, which is performed by an air furnace of which running costs is lower than that of the atmospheric furnace, reduces the time for the main-baking and thus the manufacturing cost of the sintered piece. In other words, manufacturing costs are expected to be higher when the atmosphere is controlled as compared to when an air atmosphere is used.

<2> The pre-baking allows production of high quality large sized sintered piece at low cost. The sintered piece having large size should be baked slowly and hence for a long time since otherwise the large sized sintered piece deforms and/or gets cracks due to the significant shrinkage thereof and becomes to have low quality such as inaccurate dimensions and/or low mechanical properties. If the long baking process is performed only by the atmospheric furnace, the sintered piece becomes very expensive. The pre-baking allows to bake the sintered piece slowly, so that the large size sintered piece does not deform and/or get cracks, while keeping the time for the main-baking short to reduce the manufacturing cost.

<3> The pre-baking prevents or reduces the shrinkage and hence the deformation of the molded piece during the main baking.

<4> If the main baking is performed by embedding the molded piece in a sinter assisting material, the pre-baking prevents the molded piece to be unevenly baked by the main baking. This is because the pre-baking prevents or reduces the shrinkage of the molded piece during the main baking. If the molded piece shrinks during the main baking, a gap appears between the molded piece and the sinter assisting material, which gap causes uneven baking of the embedded piece and in turn uneven mechanical strength of the sintered piece obtained. Such a gap, however, hardly appears if the molded piece is pre-baked and thus uniform baking of the molded piece during the main baking is ensured.

<5> The pre-baked molded piece has low activity. Thus, if main baking is performed by embedding the pre-baked molded piece into the sinter assisting material, adhesion/mixing of the sinter assisting material on/into the molded piece is prevented. This advantage becomes more remarkably if the sinter assisting material is also pre-baked before the main baking.

The temperature for pre-baking is preferably in a range of 900 to 1600° C., and more preferably in a range of 1050 to 1250° C. The time for pre-baking is preferably from 30 minutes to 8 hours, and more preferable from 2 to 4 hours. It should be noted, however, that the temperature and time for the pre-baking are not limited to the ranges mentioned above.

It should be noted that the pre-baking may also be performed by the atmospheric furnace instead of the air furnace. That is, the pre-baking may be performed not only in air atmosphere, but also in inert gas atmosphere (such as argon gas atmosphere and nitrogen gas atmosphere), or in oxygen atmosphere such as 25 to 100 vol % oxygen, for example.

It should be also noted that the pre-baking may be performed under the same condition as that of the main baking, which will be described later, in order to enhance the mechanical strength of the sintered piece.

Further, the pre-baking may be preformed for several times, if necessary, or may be also eliminated.

[Step S4]

In this step, main baking (second baking) of the molded piece pre-baked in step S4, or pre-baked piece, is performed.

Figure 2:
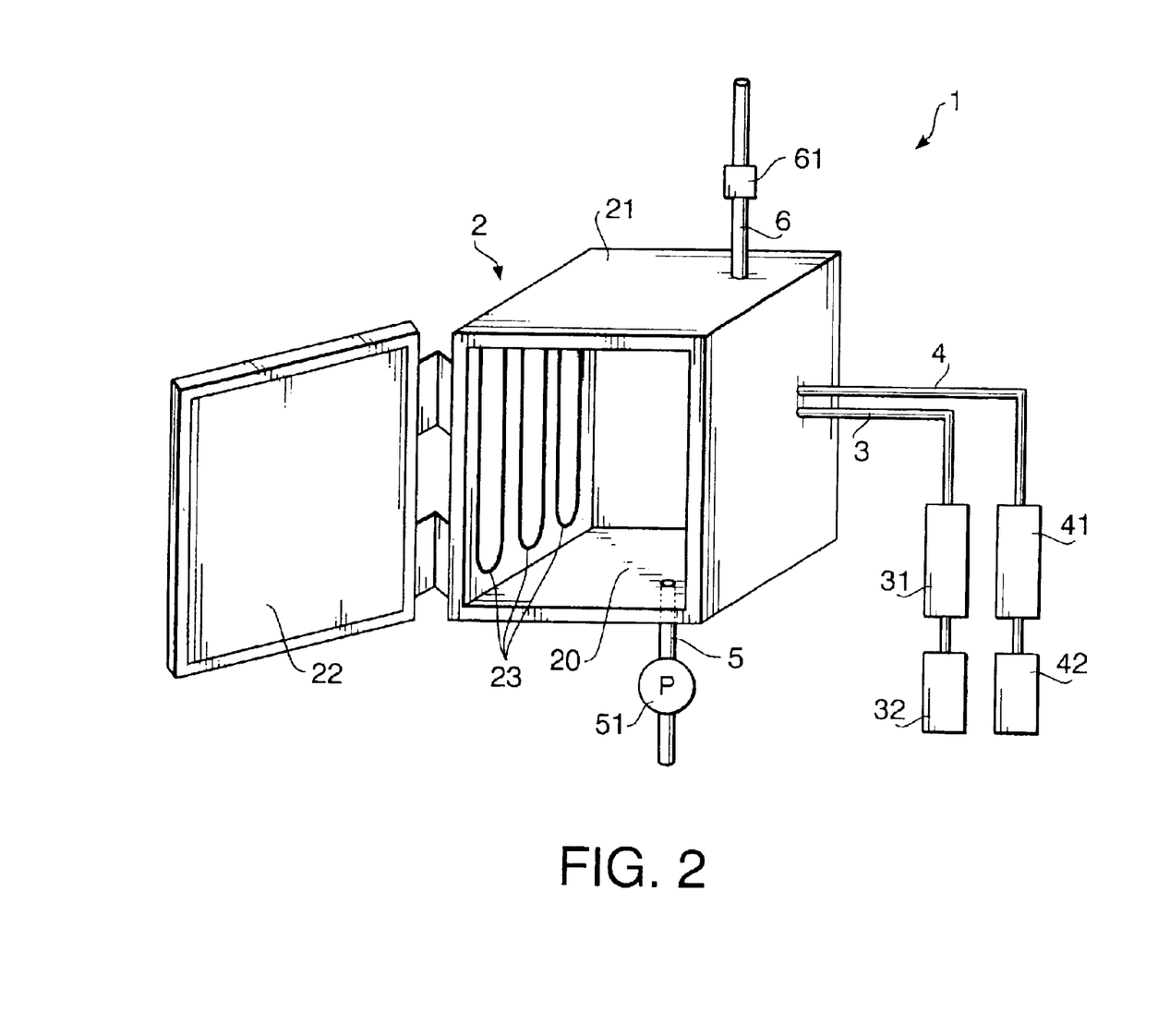
FIG. 2 schematically shows a configuration of a sintering furnace used for manufacturing the sintered piece according the embodiment of the invention.

FIG. 2 schematically shows the configuration of a sintering furnace 1 used for the main sintering of the pre-sintered piece according the embodiment of the invention.

The sintering furnace 1 includes a furnace main body 2 which has an accommodation space 20 for receiving the pre-baked piece, gas supplying lines 3 and 4 for supplying oxygen gas and argon gas (inert gas) into the accommodation space 20, respectively, a first discharging line 5 for sucking out gas or air within the accommodation space 20, and a second discharging line 6 for discharging gas from the accommodation space 20 that is introduced therein through the gas supplying lines 3 and 4.

The furnace main body 2 includes a casing 21 having a box like shape, and a substantially flat door 22 one end of which is pivotably mounted to the casing so that the door 22 swings to open and close the casing 21.

A heater 23 is equipped in the casing 21, or in the accommodation space 20, for heating the accommodation space 20 up to a temperature required for sintering the pre-baked piece.

The gas supplying lines 3 and 4 are connected to a side of the casing 21. The gas supplying lines 3 and 4 are also connected to an oxygen cylinder 32 and an argon cylinder 42, respectively, to supply oxygen gas and argon gas into the accommodation space 20.

A valve (not shown) for adjusting the gas flow rate is provided to the midway of each of the gas supplying lines 3 and 4.

The gas supplying lines 3 and 4 are further provided with drying cylinders 31 and 41, respectively, each filled with drying agent such as calcium chloride, magnesium sulfate, phosphorus pentoxide, silica gel, activated alumina, and dense sulfuric acid. Oxygen gas and argon gas are passed through the respective drying cylinder 31, 41 and thereby dried as they are supplied into the accommodation space 20 through the respective gas supplying lines 3 and 4.

The first discharging line 5 is connected to the bottom of the casing 21 (the furnace main body 2). A pump 51 is provided to the first discharging line 5 for sucking out the gas and/or air in the accommodation space 20. Note that, if one of the gas cylinders 32 or 42 is removed from the respective gas supplying line (3 and 4), then the pump can be also utilized for introducing air into the accommodation space 20.

The second discharging line 6 is connected to the top of the casing 21 (the furnace main body 2). A check valve 61 is provided to the second discharging line 6 that allows gas to flow only in the direction towards the exterior of the furnace main body 2. Thus, the gas supplied into the furnace main body 2 is gradually discharged therefrom through the second discharge line 6.

In step S4, the molded piece pre-baked in step S3 by the air furnace is further baked by the atmospheric furnace 1 described above in the following manner.

First, the pre-baked piece is placed in the accommodation space 20 within the casing 21 and the door 22 is closed to seal the accommodation space 20.

Then, the heater 23 is turned on to heat the accommodation space 20 up to a predetermined temperature, while supplying oxygen gas and argon gas through respective gas supplying line (3, 4) at a predetermined ratio. Thus, the pre-baked piece is sintered under oxygen atmosphere having a predetermined oxygen concentration. The oxygen concentration is controlled to be not less than 25 vol % and preferably to be not less that 45 vol %, since sintered piece with sufficient mechanical strength is not available, as will be described later in connection with table 1, if the main baking is performed in an oxygen atmosphere of which concentration is less than 25 vol % at about 1 atm.

The main baking is preferably performed in an atmosphere having humidity as low as possible to increase the mechanical strength of the sintered piece. Specifically, the main baking is preferably performed in an oxygen atmosphere of which relative humidity is below 30% RH, and more preferably, below 20% RH.

The temperature of the main-baking is preferably adjusted to be 1000° C. or higher, since some kinds of calcium phosphate do not sinter sufficiently at a temperature less than 1000° C., but less than the temperature at which the calcium phosphate decompose due to heat, which may result in degradation of the quality of the sintered piece. More preferably, the temperature is adjusted within a range of 1050 to 1650° C. It should be noted, however, that the temperature of the main baking is not limited to the above mentioned range.

The time for the main baking is preferably from 30 minutes to 8 hours, and more preferably, from 2 to 4 hours. It should be noted that the time for main baking varies in accordance with, for example, the baking temperature.

The main baking is preferably performed by surrounding the pre-baked piece with a sinter assisting material which serves to heat the pre-baked piece uniformly to produce a sintered piece having uniform mechanical strength.

The sinter assisting material may be provided as powder, plates, or any other suitable forms. Preferably, the sinter assisting material is provided as powder and the pre-baked piece is embedded therein during the main baking. This is because the powder allows gas to pass therethrough to the pre-baked piece embedded therein and thereby keeps the atmosphere around the pre-baked piece uniform which in turn results in production of a sintered piece having uniform mechanical strength.

Preferably, powder of which average particle diameter is within a range of 3 to 300 $\mu$m, and more preferably within a range of 10 to 80 $\mu$m, is used as the sinter assisting material. If the average diameter of the powder is less than the range mentioned above, then the powder adheres to the sintered piece and requires a large amount of time for removing it from the sintered piece. If powder of which average particle diameter is over the range mentioned above is used, it comes difficult to heat the pre-sintered piece uniformly and in turn to produce a sintered piece having uniform mechanical strength. In the course of cooling of the sintered piece after the main baking, the sintered piece releases oxygen from its surface exposing to the surrounding gas, which results in decrease of the mechanical strength of the sintered piece surface. The upper limit of the particle diameter of the sinter assisting material is also determined to keep the exposing area of the sintered piece surface small and thereby prevent significant decrease in mechanical strength thereof during the cooling.

Any material that is inert against the pre-baked piece and has sufficient heat resistance may be used as the sinter assisting material. Calcium phosphate compound and metallic oxides such as alumina, titania and kaolinite may be used as the sinter assisting material. It should be noted, however, the sinter assisting material is not limited to the above-mentioned materials.

A mixture of more than two of the above-mentioned materials may be also utilized as the sinter assisting material. A mixture having calcium phosphate compound as the main component is most preferable. In other words, a mixture having similar composition to that of the pre-baked piece is preferably used as the sinter assisting material. This is because such a mixture enhances the heat transfer efficiency between the sinter assisting material and the pre-baked piece and allows the time for baking to be reduced. The sinter assisting material having calcium phosphate compound as its main component is also advantageous in that the produced sintered piece is safe against a living body even if the sinter assisting material has contaminated or adhered to the sintered piece during the main-baking since calcium phosphate compound itself is a biomaterial.

The sinter assisting material is preferably pre-baked to decrease the activity thereof to prevent the adhesion and contamination of the sinter assisting material to the sintered piece. The sinter assisting material may be pre-baked in the previous step S3 by the air furnace together with the molded piece to reduce the total cost for producing the sintered piece.

In order to effectively prevent the adhesion and contamination of the sinter assisting material to the sintered piece, the sinter assisting material is preferably pre-baked with a temperature higher than that of the main baking.

Note that the pre-baked piece may be only partially covered with the sinter assisting material during the main-baking so that the mechanical strength thereof increases only at desired portions which may be determined in accordance with the object of the sintered piece.

As described above, the sintered piece is obtained by the steps S1 through S4. The sintered piece obtained can be used for vertebral arch spacer, artificial bones such as ear ossicle, and artificial dental root, for example.

In order to facilitate the growing of the osteoblast into the sintered piece, and to enhance the bio-compatibility of the sintered piece, the relative density of the sintered piece is preferably below 92% (void content of 8% or more), and more preferably below 85%. Further, the relative density of the sintered piece is preferably not less than 10%, and more preferably not less than 15%, since it becomes difficult to manufacture a sintered piece having practical mechanical strength if the relative density is less than 10%. It should be noted that the sintered piece produced according to the present invention maintains sufficient mechanical strength even if the void content is relatively large.

Hereinafter, some concrete examples of the manufacturing method of the sintered piece according to the invention will be described.

EXAMPLE 1

[Preparation of Slurry Including Hydroxyapatite (Calcium Phosphate Compound)]

140 g of calcium hydroxide is mixed into 1200 ml pure water within a beaker, and then, 700 ml of phosphate solution having phosphate concentration of 10 wt % is further mixed thereto to make a solution of hydroxyapatite.

The solution of hydroxyapatite is sprayed and thereby dried to obtain powder of hydroxyapatite having an average particle diameter of 18 $\mu$m.

Next, the powder obtained is baked for 4 hours at a temperature of 700° C. Then, the baked powder is crushed to obtain hydroxyapatite powder having an average particle diameter of 16 $\mu$m.

Finally, the hydroxyapatite powder is mixed with pure water at a mixing ratio of powder to water, based on weight, of 5 to 6.

[Molding of Hydroxyapatite]

The slurry of the hydroxyapatite is brought into a molding tool of which inner surface is applied with liquid paraffin. Then, the slurry is dried at a temperature of 40° C. for two days (48 hours). After the drying, the molded piece is removed from molding tool and cut into a test piece which is 32 mm long, 17 mm wide and 5 mm thick.

[Pre-Baking of the Test Piece]

The test piece is baked for 4 hours at a temperature of 1200° C. in air of which relative humidity is 50% RH and the oxygen concentration is 20 vol % at about 1 atm. In this way, a pre-baked test piece having a relative density of 70% is obtained.

The pre-baked test piece is further ground by a diamond file to a size of 30 mm long, 15 mm wide, and 3 mm thick.

Light of a halogen lamp (wavelength 375–4000 nm, power 85 W) is illuminated on the backside of the pre-baked test piece through an optical fiber, which is 30 cm long, and has a diameter of 4 mm. The brightness and the chromaticity of the light that has transmitted through the test piece are measured by chromoscope (type CS-100 available from Minolta) placed at 35 cm apart from the pre-baked test piece. The measured brightness of the transmitted light is 200 cd/m$^2$ and the chromaticity thereof is within a range defined by $-20/23x+79/92 \geq y > -20/23x+359/460$ on the CIE chromaticity diagram.

[Main-Baking of the Test Piece]

The test piece is embedded in powder of hydroxyapatite, or the sinter assisting material, having an average particle diameter of 20 $\mu$m and then placed in the casing 21 of the atmospheric furnace 1 shown in FIG. 2. Note that the hydroxyapatite powder is previously pre-baked for 4 hours at a temperature of 1200° C.

Then, the test piece is baked for two hours at a temperature of 1200° C. under oxygen atmosphere of which oxygen concentration is 100 vol % (at about 1 atm) and the relative humidity is 3% RH. As a result, a sintered test piece having almost the same dimensions as that of the pre-baked test piece is obtained. The relative density of the sintered test piece is 71%.

The brightness and chromaticity of a light transmitted through the sintered test piece is measured in the same way as that of the pre-baked test piece. The measured brightness is 5 cd/m$^2$ and the chromaticity is at (0.66, 0.33) on the CIE chromaticity diagram which is within the area defined by $y \geq -20/23x+1999/2300$ (see FIG. 3).

The whole test piece has a color of reddish brown. An X-ray diffraction pattern of powder obtained by crushing the reddish brown color portion of the test piece, which is measured by an X-ray diffractometer (type RINT 2000 available from Rigaku company) does not indicate any peak of which intensity is larger than 0.5% of the main peak within a range of $36.5° \geq 2\theta \geq 36°$ (see FIG. 3).

EXAMPLE 2

In this example, the test piece is prepared by in the same manner as that of the example 1 except that the relative humidity of the oxygen atmosphere of the main baking is controlled to 25% RH instead of 3% RH. The properties of the pre-baked test piece and the sintered test-piece of the present example are as followings.

| | Pre-Baked Test Piece |
|---|---|
| Relative Density: | 75% |
| Brightness of the Transmitted Light: | 40 cd/m$^2$ |
| Chromaticity of the Transmitted Light: | Within the area defined by $-20/23x + 79/92 > y \geq -20/23x + 359/460$ |

| Sintered Test Piece | |
|---|---|
| Relative Density: | 75% |
| Brightness of the Transmitted Light: | 3 cd/m² |
| Chromaticity of the Transmitted Light: | (0.66, 0.33) on the CIE chromaticity diagram which is within the area defined by y ≧ −20/23x + 1999/2300 |

Further, the whole surface of the sintered test piece has a reddish brown color and the X-ray diffraction pattern of the powder obtained by crushing the reddish brown color portion does not have any peak of which intensity is larger than 0.5% of the main peak within a range of 36.5°≧2θ≧36°.

EXAMPLE 3

In this example, the test piece is prepared in the same manner as that of the example 1 except that oxygen atmosphere of the main-baking is controlled to have oxygen concentration of 50 vol % (oxygen 50 vol %+argon 50 vol %) at about 1 atm and relative humidity of 25% RH instead of oxygen concentration of 100 vol % at about 1 atm and relative humidity of 3% RH. The properties of the pre-baked test piece and the sintered test-piece of the present example are as followings.

| Pre-baked Test Piece | |
|---|---|
| Relative Density: | 74% |
| Brightness of the Transmitted Light: | 75 cd/m² |
| Chromaticity of the Transmitted Light: | Within the area defined by −20/23x + 79/92 > y ≧ −20/23x + 359/460 |

| Sintered Test Piece | |
|---|---|
| Relative Density: | 76% |
| Brightness o the Transmitted Light: | 55 cd/m² |
| Chromaticity of the Transmitted Light: | (0.59, 0.38) on the CIE chromaticity diagram which is within the area defined by y ≧ −20/23x + 1999/2300 |

Further, the whole surface of the sintered test piece has a yellow white color and the X-ray diffraction pattern of powder obtained by crushing the yellow white color portion does not have any peak of which intensity is larger than 0.5% of the main peak within a range of 36.5°≧2θ≧36°.

EXAMPLE 4

In this example, the test piece is prepared in the same manner as that of the example 1 except that the pre-baking is performed in oxygen atmosphere of 50 vol % (oxygen 50 vol %+argon 50 vol %) having relative humidity of 3% RH instead of in air having relative humidity of 50% RH. The properties of the pre-baked test piece and the sintered test-piece of the present example are as followings.

| Pre-baked Test Piece | |
|---|---|
| Relative Density: | 75% |
| Brightness of the Transmitted Light: | 190 cd/m² |
| Chromaticity of the Transmitted Light: | Within the area on the CIE chromaticity diagram defined by −20/23x + 79/92 > y ≧ −20/23x + 359/460 |

| Sintered Test Piece | |
|---|---|
| Relative Density: | 76% |
| Brightness of the Transmitted Light: | 45 cd/m² |
| Chromaticity of the Transmitted Light: | (0.59, 0.38) on the CIE chromaticity diagram which is with in the area defined by y ≧ −20/23x + 1999/2300 |

Further, the whole surface of the sintered test piece has a yellow white color and the X-ray diffraction pattern of powder obtained by crushing the yellow white color portion does not have any peak of which intensity is larger than 0.5% of the main peak within a range of 36.5°≧2θ≧36°.

EXAMPLE 5

In this example, the test piece is prepared in the same manner as that of the example 1 except that the pre-baking is omitted. The properties of the sintered test-piece of the present example are as followings.

| Sintered Test Piece | |
|---|---|
| Relative Density: | 75% |
| Brightness of the Transmitted Light: | 6 cd/m² |
| Chromaticity of the Transmitted Light: | (0.66, 0.33) on the CIE chromaticity diagram which is within the are defined by y ≧ −20/23x + 1999/2300 |

Further, the whole surface of the sintered test piece has a reddish brown color and the X-ray diffraction pattern of powder obtained by crushing the reddish brown color portion does not have any peak of which intensity is larger than 0.5% of the main peak within a range of 36.5°≧2θ≧36°.

EXAMPLE 6

In this example, the test piece is prepared in the same manner as that of the example 1 except that the pre-baking is omitted and that the main-baking is performed by placing the molded piece on an alumina plate instead of embedding it into the sinter assisting material. The properties of the sintered test-piece of the present example are as followings.

| Sintered Test Piece | |
|---|---|
| Relative Density: | 74% |
| Brightness of the Transmitted Light: | 10 cd/m² |

-continued

| Sintered Test Piece | |
|---|---|
| Chromaticity of the Transmitted Light: | (0.66, 0.33) on the CIE chromaticity diagram which is within the area defined by $y \geq -20/23x + 1999/2300$ |

Further, the whole surface of the sintered test piece has a reddish brown color and the X-ray diffraction pattern of powder obtained by crushing the reddish brown color portion does not have any peak of which intensity is larger than 0.5% of the main peak within a range of $36.5° \geq 2\theta \geq 36°$.

EXAMPLE 7

[Preparation of Slurry Including Hydroxyapatite (Calcium Phosphate Compound)]

140 g of calcium hydroxide is mixed into 1200 ml pure water in a beaker, and then, 700 ml of phosphate solution having phosphate concentration is 10 wt % is further mixed dropped thereinto. Then, the solution in the beaker is stirred to obtain a solution of hydroxyapatite.

The solution of hydroxyapatite is sprayed and thereby dried to make powder of hydroxyapatite having an average particle diameter of 18 μm.

The powder obtained is baked for 4 hours at a temperature of 700° C. Then, the baked powder is crushed to obtain hydroxyapatite powder having an average particle diameter of 15 μm.

Next, the hydroxyapatite powder is mixed with methylcellulose solution (1 wt %) by using a whisk to obtain a slurry including foam. The mixing ratio between the hydroxyapatite powder and the methylcellulose solution is one to two (weight ratio).

[Molding of Hydroxyapatite]

The slurry of the hydroxyapatite is brought into a molding tool of which inner surface is applied with liquid paraffin. Then, the slurry is dried by heating it at 80° C. for five days (120 hours). After the drying, the molded piece is taken out from the molding tool and cut into a test piece which is 36.4 mm long, 11.2 mm wide and 11.2 mm thick.

[Pre-Baking of the Test Piece]

The test piece is baked for 4 hours at 1200° C. in air having relative humidity of 50% RH and oxygen concentration of 20 vol % at about 1 μm. In this way, a pre-baked test piece having a relative density of 55% is obtained.

The pre-baked test piece is further ground by a diamond file to a size of 26 mm long, 8 mm wide, and 8 mm thick.

Light of a halogen lamp (wavelength 375–4000 nm, power 85 W) is illuminated on the backside of the pre-baked test piece through an optical fiber, which is 30 cm long, and has a diameter of 4 mm. The brightness of the light that has transmitted through the test piece is measured by chromoscope (type CS-100 available from Minolta) placed at 35 cm apart from the pre-baked test piece. The measured brightness of the transmitted light is 115 cd/m².

[Main-Baking of the Test Piece]

The test piece is embedded in powder of hydroxyapatite, or the sinter assisting material, having an average particle diameter of 20 μm and then placed in the casing 21 of the atmospheric furnace 1 shown in FIG. 2. Note that the hydroxyapatite powder is previously pre-baked for 4 hours at 1200° C.

Then, the test piece is baked for two hours at 1200° C. under oxygen atmosphere having oxygen concentration of 50 vol % (oxygen 50 vol %+argon 50 vol %, at about 1 atm) and relative humidity of 3% RH. As a result, a sintered test piece having almost the same dimension as that of the pre-baked test piece is obtained. The relative density of the sintered test piece is 56%.

The brightness of a light transmitted through the sintered test piece is measured in the same way as that of the pre-baked test piece. The measured brightness is 1 cd/m².

The whole test piece is colored in yellow white. The X-ray diffraction pattern of powder obtained by crushing the yellow white color portion does not indicate any peak of which intensity is larger than 0.5% of the main peak within a range of $36.5° \geq 2\theta \geq 36°$.

COMPARATIVE EXAMPLE 1

In this example, the test piece is prepared in the same manner as that of the example 1 except that the main-baking is performed in air having relative humidity of 50% RH and oxygen concentration of 20 vol % (at about 1 atm) instead of in oxygen atmosphere having relative humidity of 3% RH and oxygen concentration of 100 vol %, and that the pre-baked test piece is placed on an alumina plate instead of being embedded into powder of the sinter assisting material. The properties of the pre-baked test piece and the sintered test-piece of the present example are as followings.

| Pre-baked Test Piece | |
|---|---|
| Relative Density: | 75% |
| Brightness of the Transmitted Light: | 180 cd/m² |
| Chromaticity of the Transmitted Light: | within the area defined by $-20/23x + 79/92 > y \geq -20/23x + 359/460$ |

| Sintered Test Piece | |
|---|---|
| Relative Density: | 76% |
| Brightness of the Transmitted Light: | 175 cd/m⁺ |
| Chromaticity of the Transmitted Light: | (0.55, 0.31) on the CIE chromaticity diagram which is within an area defined by $-20/23x + 79/92 > y \geq -20/23x + 1999/2300$ |

Figure 5:
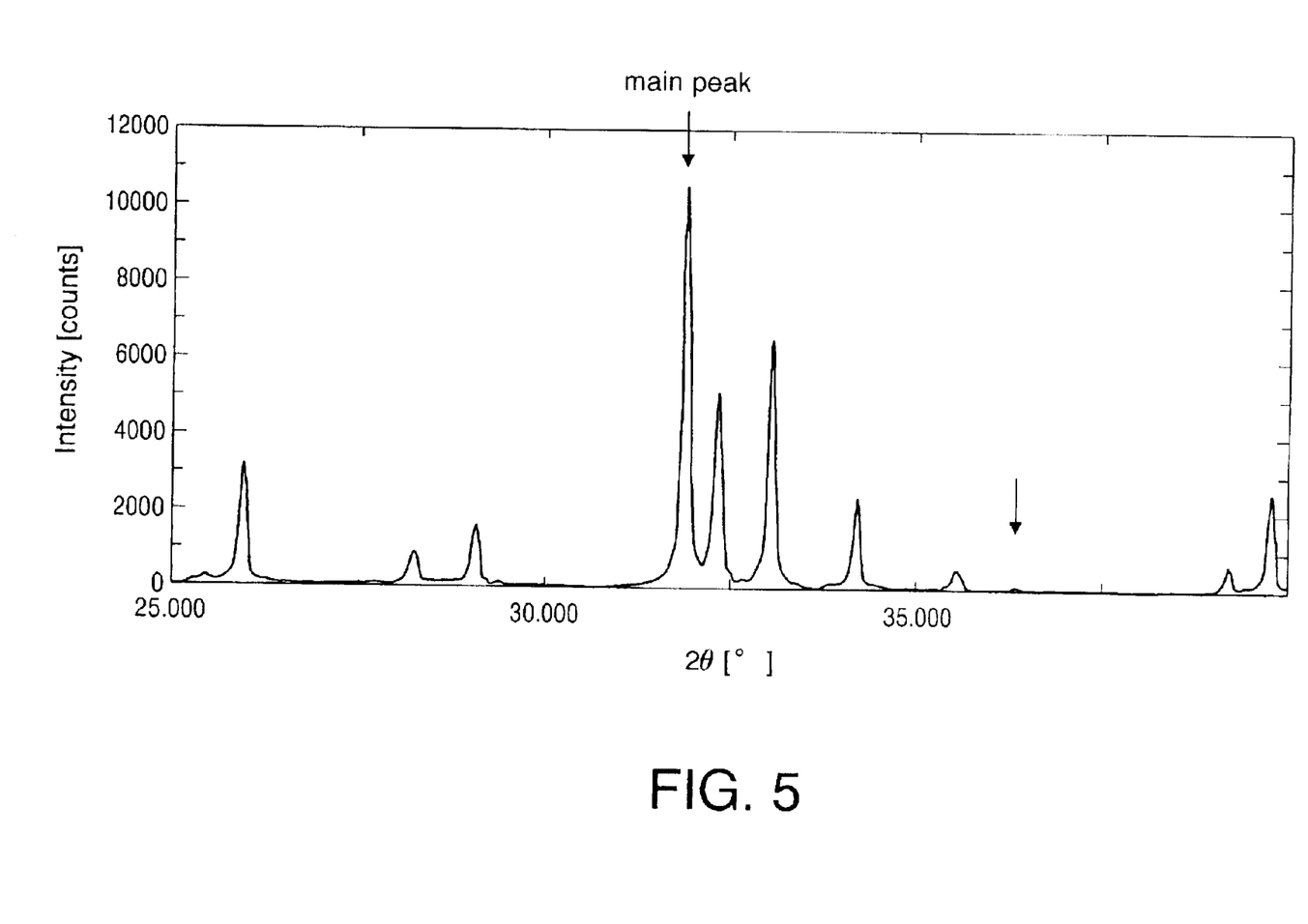
FIG. 5 is an X-ray diffraction pattern of powder obtained by crushing a sintered piece prepared by a method different from that of the invention.

Further, the whole surface of the sintered test piece has a light pink color and does not have any portion colored in reddish brown or the like. The X-ray diffraction pattern of powder obtained by crushing a portion about the center of the test piece shows a peak of which intensity is larger than 0.5% of the main peak within a range of $36.5° \geq 2\theta \geq 36°$ (see FIG. 5).

COMPARATIVE EXAMPLE 2

In this example, the test piece is prepared in the same manner as that of the example 1 except that the main-baking is performed in an argon atmosphere of which argon concentration is 100 vol % (at about 1 atm) and relative humidity is 3% instead in the oxygen atmosphere having oxygen concentration of 100 vol % and relative humidity of 3%. The properties of the pre-baked test piece and the sintered test-piece of this example are as followings.

| Pre-baked Test Piece | |
|---|---|
| Relative Density: | 75% |
| Brightness of the Transmitted Light: | 180 cd/m² |
| Chromaticity of the Transmitted Light: | within the area defined by $-20/23x + 79/92 > y \geq -20/23x + 359/460$ |

| Sintered Test Piece | |
|---|---|
| Relative Density: | 75% |
| Brightness of the Transmitted Light: | 250 cd/m² |
| Chromaticity of the Transmitted Light: | (0.47, 0.40) on the CIE chromaticity diagram which is within the area defined by $-20/23x + 79/92 > y \geq -20/23x + 359/460$ |

Further, the whole surface of the sintered test piece has white color and does not have any portion colored in reddish brown or the like. The X-ray diffraction pattern of powder obtained by crushing a portion about the center of the test piece shows a peak of which intensity is larger than 0.5% of the main peak within a range of $36° \geq 2\theta \geq 36.5°$.

COMPARATIVE EXAMPLE 3

In this example, the test piece is prepared in the same manner as that of the example 7 except that the main-baking is performed in air of which relative humidity is 25% and oxygen concentration is 20 vol % (at about 1 atm) instead of in the oxygen atmosphere of which oxygen concentration is 50 vol % and relative humidity is 3% RH, and that the pre-baked test piece is placed on an alumina plate instead of being embedded into powder of the sinter assisting material. The properties of the pre-baked test piece and the sintered test-piece of the present example are as followings.

| Pre-baked Test Piece | |
|---|---|
| Relative Density: | 55% |
| Brightness of the Transmitted Light: | 80 cd/m² |

| Sintered Test Piece | |
|---|---|
| Relative Density: | 55% |
| Brightness of the Transmitted Light: | 65 cd/m² |

Further, the whole surface of the sintered test piece has light pink color and does not have any portion colored in reddish brown or the like. The X-ray diffraction pattern of powder obtained by crushing a portion about the center of the test piece shows a peak of which intensity is larger than 0.5% of the main peak within a range of $36° \geq 2\theta \geq 36.5°$.

Mechanical Strength of the Test Pieces

The mechanical strength of each of the sintered test pieces obtained in the examples 1 through 7 and the comparative examples 1 through 3 is measured by executing three point bending test performed in accordance with Japanese Industrial Standards (JIS) R 1601. Table 1 shows the baking conditions of the test pieces as well as the properties thereof including the mechanical strength measured by the above-mentioned three point bending test.

TABLE 1

| | Condition of Pre-baking | | Use of Sintering Supplemental Material | Condition of Main-baking | | Properties of Sintered Test Piece | | | | Mech. Strength [kgf/cm²] |
|---|---|---|---|---|---|---|---|---|---|---|
| | Atmosphere | Temp. × Time | | Atmosphere | Temp. × Time | Relative Density [%] | Transmitted Light | | Color | |
| Example 1 | Air 50% RH | 1200° C. × 4 h | Yes | O₂ 100 vol % 3% RH | 1200° C. × 2 h | 71 | Chromaticity | (0.66, 0.33) | R.B. (whole) | 498 |
| Example 2 | Air 50% RH | 1200° C. × 4 h | Yes | O₂ 100 vol % 25% RH | 1200° C. × 2 h | 75 | | (0.66, 0.33) | R.B. (whole) | 502 |
| Example 3 | Air 50% RH | 1200° C. × 4 h | Yes | O₂ 50 vol % 25% RH | 1200° C. × 2 h | 76 | | (0.59, 0.38) | Y.W. (whole) | 503 |
| Example 4 | O₂ 50 vol % 3% RH | 1200° C. × 4 h | Yes | O₂ 100 vol % 3% RH | 1200° C. × 2 h | 76 | | (0.59, 0.38) | Y.W. (whole) | 505 |
| Example 5 | — | | Yes | O₂ 100 vol % 3% RH | 1200° C. × 2 h | 75 | | (0.66, 0.33) | R.B. (whole) | 490 |
| Example 6 | — | | No | O₂ 100 vol % 3% RH | 1200° C. × 2 h | 74 | | (0.66, 0.33) | R.B. (interior) | 485 |
| Example 7 | Air 50% RH | 1200° C. × 4 h | Yes | O₂ 50 vol % 3% RH | 1200° C. × 2 h | 56 | Brightness [cd/m²] | 1 | Y.W. (whole) | 115 |
| Comparative Example 1 | Air 50% RH | 1200° C. × 4 h | No | Air 50% RH | 1200° C. × 2 h | 76 | Chromaticity | (0.55, 0.31) | L.P. (whole) | 464 |
| Comparative Example 2 | Air 50% RH | 1200° C. × 4 h | No | Ar 100 vol % 3% RH | 1200° C. × 2 h | 75 | | (0.47, 0.40) | white (whole) | 450 |
| Comparative Example 3 | Air 50% RH | 1200° C. × 4 h | No | Air 25% RH | 1200° C. × 2 h | 55 | Brightness [cd/m²] | 65 | L.P. (whole) | 101 |

R.B.: reddish brown
Y.W.: yellow white
L.P.: light pink

As shown in table 1, the sintered test pieces of the examples 1 through 6 have better mechanical strength than those of the comparative examples 1 and 2 although the relative densities of these test pieces are almost same. Further, the test piece of example 7 also shows better mechanical strength than that of the test piece obtain in comparative example 3 although the relative densities of these test pieces are also almost the same.

From the properties of the test pieces obtained in the above-mentioned examples and comparative examples, it is found that the sintered piece shows excellent mechanical strength when one of the following four conditions is satisfied.

Figure 3:
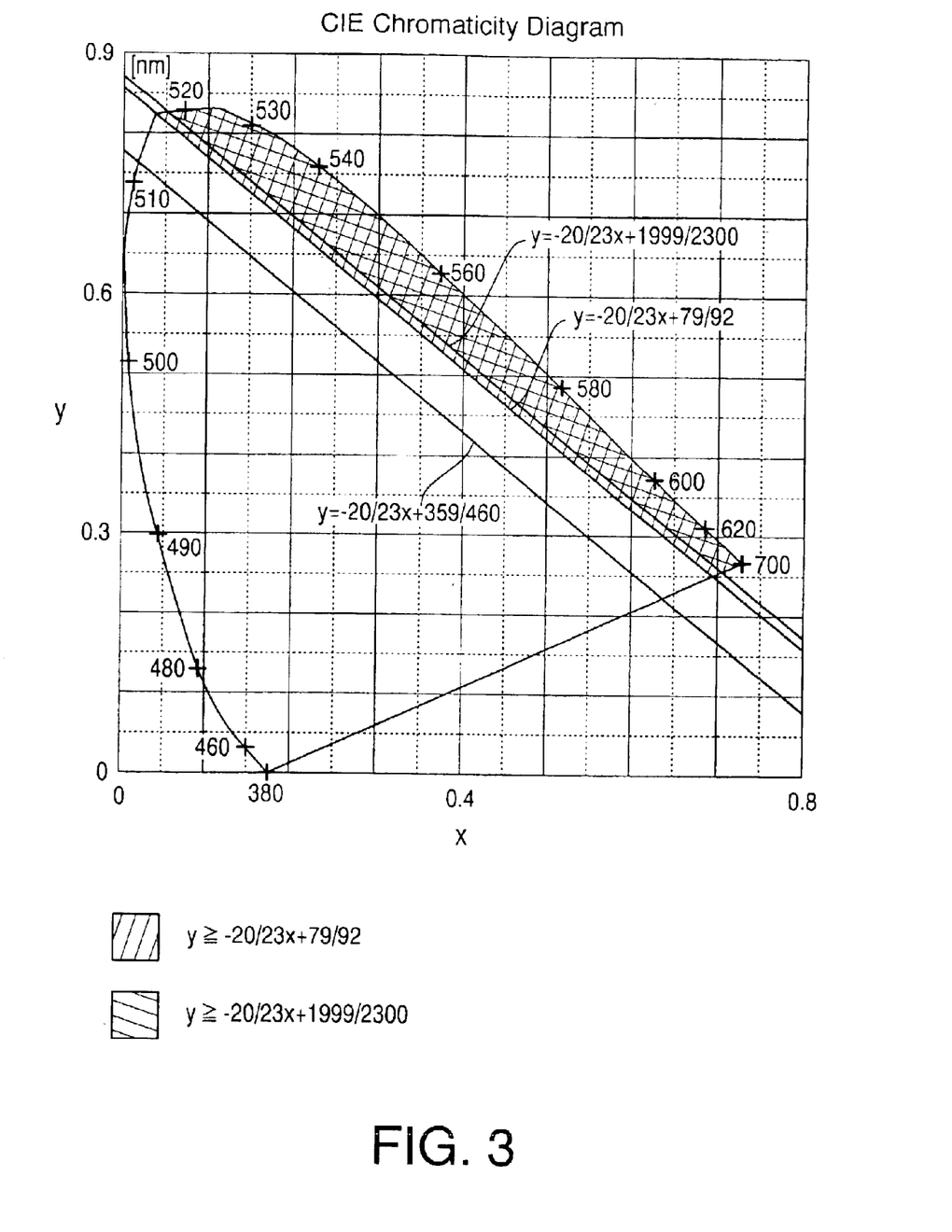
FIG. 3 shows an example of a chromaticity diagram indicating the color area of a light that has transmitted through a test piece prepared by the manufacturing method according to the embodiment of the invention.
Figure 4:
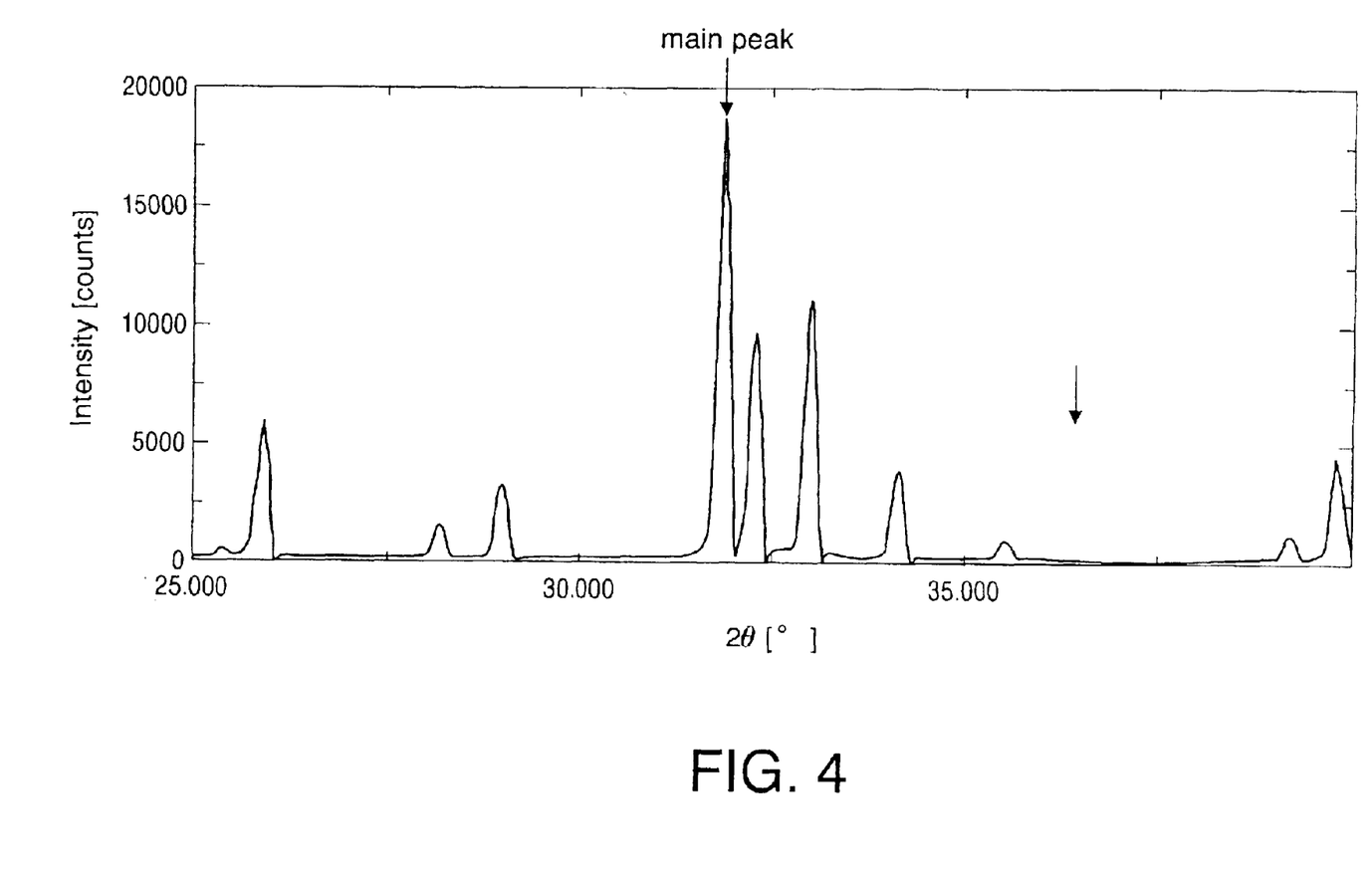
FIG. 4 is an X-ray diffraction pattern of powder obtained by crushing a sintered piece prepared by the manufacturing method according to the embodiment of the invention.

(1) When a light from a 85 W halogen lamp is applied, through an optical fiber which is 30 cm long and 4 mm in diameter, on a test piece of the sintered piece, which is 3 mm thick and of which relative density is within a range of 67 to 77%, the light that has transmitted through the test piece has a color which is within an area defined by $y \geq -20/23x+79/92$, and more specifically, $y \geq -20/23x+1999/2300$ on the CIE chromaticity diagram (see FIG. 3).

(2) When a light from a 85 W halogen lamp is applied through an optical fiber, which is 30 cm long and 4 mm in diameter, on a test piece of the sintered piece, which is 8 mm thick and of which relative density is in a range of 45 to 55%, the light that has transmitted through the test piece has a brightness of less than 15 cd/m$^2$, and more specifically 10 cd/m$^2$.

(3) The sintered piece includes a colored portion of which color (yellow white, reddish brown, gray or black, for example) is different from the color of the molded piece, or the piece before being baked (which is generally white or light pink).

(4) The X-ray diffraction pattern of the powder obtained by crushing the colored portion of the sintered piece does not have any peak of which intensity is larger than 0.5% of the main peak intensity within a range $36° \geq y \geq 36.5°$.

The present disclosure relates to the subject matter contained in Japanese Patent Application No. P2001-347984, filed on Nov. 13, 2001, which is expressly incorporated herein by reference in its entirety.

What is claimed is:

1. A method for manufacturing a sintered piece, comprising:

molding a composite including calcium phosphate compound to form a molded piece; and baking the molded piece in an oxygen atmosphere to obtain the sintered piece, the oxygen atmosphere having an oxygen concentration of not less than 25 vol %.

2. The method according to claim 1, wherein the oxygen atmosphere has a relative humidity below 30% RH.

3. The method according to claim 1, wherein said baking is performed at a temperature not less than 1000° C. and below a temperature at which thermal decomposition of the calcium phosphate occurs.

4. The method according to claim 1, wherein said baking is performed for 30 minutes to 8 hours.

5. The method according to claim 1, wherein at least a part of the molded piece is covered with a sinter assisting material during the baking.

6. The method according to claim 5, wherein the sinter assisting material is provided as powder.

7. The method according to claim 6, wherein the powder has an average particle diameter of 3 μm to 300 μm.

8. The method according to claim 5, wherein a main component of the sinter assisting material is calcium phosphate compound.

9. The method according to claim 8, further comprising pre-baking the sinter assisting material in advance of the baking of the molded piece, the pre-baking being performed at a temperature not less than the temperature of the baking.

10. The method according to claim 1, further comprising pre-baking the molded piece in advance of the baking.

11. The method according to claim 10, wherein the pre-baking and the baking of the molded piece is performed under different conditions.

12. The method according to claim 1, wherein chromaticity of a light that has transmitted the sintered piece is within an area of $y \geq -20/23x+79/92$ on a CIE chromaticity diagram, the light being emitted from a 85 W halogen lamp and illuminated on the sintered piece through an optical fiber being 4 mm in diameter and 30 cm long, the sintered piece being 3 mm thick and having relative density of 67% to 77%.

13. The method according to claim 1, wherein brightness of a light that has transmitted the sintered piece is below 15 cd/m$^2$, the light being emitted from a 85 W halogen lamp and illuminated on the sintered piece through an optical fiber being 4 mm in diameter and 30 cm long, the sintered piece being 8 mm thick and having relative density of 45% to 55%.

14. The method according to claim 1, wherein the sintered piece includes a colored part of which color is different from a color of the molded piece.

15. The method according to claim 14, wherein an X-ray diffraction pattern of powder obtained by crushing the colored part of the sintered piece does not include a peak larger than 0.5% of a main peak thereof within a range of $36.5° \geq 2\theta \geq 36°$.

16. The method according to claim 1, wherein the sintered piece has a relative density below 92%.

17. The method according to claim 1, wherein the calcium phosphate compound is hydroxyapatite.

* * * * *